United States Patent [19]

Burk

[11] Patent Number: 5,596,114

[45] Date of Patent: Jan. 21, 1997

[54] CHIRAL PHOSPHOLANES VIA CHIRAL 1 4-DIOL CYCLIC SULFATES

[75] Inventor: Mark J. Burk, Hockessin, Del.

[73] Assignee: E. I. Du Pont de Nemours and Company, Wilmington, Del.

[21] Appl. No.: 449,439

[22] Filed: May 24, 1995

Related U.S. Application Data

[62] Division of Ser. No. 324,329, Oct. 17, 1994, abandoned, which is a division of Ser. No. 222,750, Apr. 4, 1994, Pat. No. 5,386,061, which is a division of Ser. No. 978,215, Jul. 27, 1992, Pat. No. 5,329,015, which is a division of Ser. No. 725,121, Jul. 2, 1991, Pat. No. 5,171,892.

[51] Int. Cl.$^6$ .................................................. C07F 9/50
[52] U.S. Cl. ............................................. 556/22; 568/12
[58] Field of Search ............................... 568/12; 556/21, 556/22

[56] References Cited

U.S. PATENT DOCUMENTS

| | | | |
|---|---|---|---|
| 4,724,101 | 2/1988 | Fellmann et al. | 556/22 |
| 4,924,007 | 5/1990 | Massonneau et al. | 549/18 |
| 4,960,904 | 10/1990 | LeRoy et al. | 549/34 |
| 5,008,457 | 4/1991 | Burk | 568/12 |
| 5,021,131 | 6/1991 | Burk | 204/59 R |
| 5,171,892 | 12/1992 | Burk | 568/12 |
| 5,466,844 | 11/1995 | Spindler et al. | 556/22 |

FOREIGN PATENT DOCUMENTS

| | | | |
|---|---|---|---|
| 2-273626 | 11/1990 | Japan | C07B 39/00 |
| 944406 | 12/1963 | United Kingdom . | |

OTHER PUBLICATIONS

Burk, M. J. et al, *Organometallics*, 9(10), 2653–2655 (1990).
Burk, M. J. et al, *Angewandte Chemie.*, 29(12), 1462–1464 (1990).
Gao, Y. et al, *J. Am. Chem. Soc.*, 110, 7538–7539 (1988).
Kim, B. M. et al, *Tetrahedron Ltrs.*, 30(6), 655–658 (1989).
Lloyd, E. J. et al, *Aust. J. Chem.*, 30, 569–578 (1977).
Machinaga, N. et al, *Tetrahedron Ltrs.*, 31(25), 3637–3640 (1990).
Brunner, H. et al, *J. of Organometallic Chem.*, 328, 71–80 (1987).
Wilson, S. R. et al, *Synlett*, 199–200 (Apr. 1990).
Lichtenberger, J. et al, *Bull. Chim. soc. Fr.*, p. 1495 (1961).
Denney, D. B. et al, *J. Am. Chem. Soc.*, 94(1), 245–249 (1972).
Hitchcock, P. B. et al, *J. Chem. Soc., Chem. Comm.*, 1598–1599 (1992).
Burk, M. J., *J. Am. Chem. Soc.*, 113, 8518–8519 (1991).
Kim, T. J., *Chemical Abstracts*, 106, p. 679, Abstract No. 21401q (1987).
*Chemical Abstracts*, 106, Part 2, p. 1855RP, Abstract No. 108280-65-5 (1987).
Machinaga, N. et al, *J. Org. Chem.*, 56(4), 1386–1393 (1991).

*Primary Examiner*—Robert W. Ramsuer
*Assistant Examiner*—John Peabody

[57] ABSTRACT

Novel chiral 1,4-diol cyclic sulfates and their use as precursors in the preparation of chiral phospholane ligands, and chiral complexes useful as catalysts for carrying out enantioselective reactions.

5 Claims, No Drawings

5,596,114

CHIRAL PHOSPHOLANES VIA CHIRAL 1 4-DIOL CYCLIC SULFATES

This is a division of application Ser. No. 08/324,329, filed Oct. 17, 1994, now abandoned; which is a division of application Ser. No. 08/222,750 filed Apr. 4, 1994, issued as U.S. Pat. No. 5,386,061; which is a divisional of application Ser. No. 07/978,215 filed Jul. 27, 1992, issued as U.S. Pat. No. 5,329,015; which is a division of application Ser. No. 07/725,121 filed Jul. 2, 1991, issued as U.S. Pat. No. 5,171,892.

FIELD OF THE INVENTION

The invention relates to novel chiral 1,4-diol cyclic sulfates and their use as precursors in the preparation of chiral phosphines, including novel chiral bis(phospholanes). Chiral transition metal complexes of these chiral bis(phospholanes) are efficient catalysts for carrying out enantioselective reactions.

BACKGROUND OF THE INVENTION

The development of novel catalytic systems exhibiting unique reactivity and high enantioselectivity requires the synthesis of chiral ligands for transition metals. Generally, some of the most successful chiral ligands have been chelating phosphines possessing a $C_2$ symmetry axis.

Many of the chiral phosphines known in the art have at least two aryl substituents on the phosphorous, rendering that center relatively electron poor. The mechanism of asymmetric induction using these phosphines has been linked to the proper conformational relationship between the phenyl groups on the phosphorous centers.

More recently, chiral phosphines having relatively electron rich phosphorus centers have been reported. Brunner et al., Journal of Organometallic Chemistry, Vol. 328, pp 71–80 (1987) teach 3,4-disubstituted phospholanes derived from tartaric acid having chloro, methoxy, or dimethylamino substituents. These were complexed with manganese and rhodium and used as catalysts in the hydrogenation of alpha-N-acetamidocinnamic acid. Relatively low optical yields of (S)-N-acetylphenylalanine of from 6.6% enantiomeric excess to 16.8% enantiomeric excess were obtained.

S. R. Wilson and A. Pasternak, Synlett, pp. 199–200, April 1990 describe the preparation of (2R,5R)-1-phenyl-2,5-dimethylphospholane and its use in an enantioselective Staudinger reaction (reduction of azides with phosphines). Here the chiral (2R,5R)-1-phenyl-2,5-dimethylphospholane is used as a stoichiometric reactant, not as a catalyst.

M. J. Burk et al, Organometallics, Vol 9, pp. 2653–2655 (1990) describe a series of mono and bidentate 2,5-disubstituted phospholanes and demonstrate their use as ligands in asymmetric catalysis. Rhodium complexes bearing the disclosed phosphine ligands were prepared and tested as catalyst precursors for the enantioselective hydrogenation of unsaturated substrates. The phosphorous atoms in the disclosed bis phospholanes are linked by two- or three-carbon methylene bridges.

M. J. Burk et al, Angewandte Chemie, International Edition in English, Vol 29, pp 1462–1464 (1990) disclose tris phospholane tridentate ligands with $C_3$ symmetry.

U.S. Pat. No. 5,008,457 issued Apr. 16, 1991, discloses mono, bidentate, and tridentate phospholanes useful as transition metal ligands in asymmetric catalysis and processes for their preparation as in the above two Burk et al. references.

Several references teach various synthetic routes for the preparation of cyclic sulfites or cyclic sulfates. However, these contain no disclosure nor suggestions that the disclosed reaction sequence could be used to prepare symmetrical chiral 1,4-diol derived cyclic sulfites or 1,4-diol derived cyclic sulfates.

Y. Gao and K. B. Sharpless, J. Am. Chem. Soc., 110, 7538(1988) disclosed the reaction of 1,2-diols, including some chiral 1,2-diols, with thionyl chloride to form 5-membered ring cyclic sulfites which, upon oxidation with $NaIO_4$ and catalytic $RuC_{l3,}$ are converted to 5-membered ring cyclic sulfates.

B. M. Kim and K. B. Sharpless, Tetrahedron Lett., 30, 655(1989) report further on the preparation and reactivity of 5-membered ring cyclic sulfates derived from 1,2-diols.

U.S. Pat. No. 4,924,007 discloses a process for the preparation of 5- and 6-membered ring cyclic sulfates from 1,2- and 1,3-diols by reaction with concentrated sulfuric acid at 150° C. to 250° C.

U.S. Pat. No. 4,960,904 discloses a process for the preparation of 5- and 6-membered ring cyclic sulfates from 5- and 6-membered ring cyclic sulfites by oxidation.

Great Britain Patent 944,406 discloses a process for the preparation of 5- and 6-membered ring cyclic sulfates from 1,2- and 1,3-diols by reaction with first, thionyl chloride to form 5- and 6-membered ring cyclic sulfites and second, an oxidizing agent.

J. Lichtenberger and J. Hincky, Bull. Chim. Soc. Fr, 1495(1961) describe the synthesis of a cyclic sulfate from 1,4-butanediol.

E. J. Lloyd and Q. N. Porter, Aust. J. Chem., 30, 569(1977) describe the syntheses of cyclic sulfates from 1,4-butanediol and 2,5-hexanediol.

N. Machinaga and C. Kibayashi, Tetrahedron Letters, Vol. 31, p. 3637 (1990), describe the synthesis of an unsymmetrical, chiral 1,4-diol derived cyclic sulfate and the synthesis of an unsymmetrical, chiral 2,5-disubstituted pyrrolidine from it.

A continuing need exists for transition metal complexes providing high levels of stereochemical control and asymmetric induction in stoichiometric and catalytic transformations. A need also exists for chiral ligands having a high degree of enantiomeric purity for use in the preparation of transition metal catalysts, and for efficient synthetic routes for the preparation of such chiral ligands.

It therefore an object of the present invention to provide cyclic sulfate compounds for use in preparation of chiral bis(phospholane) ligands.

It is a further object of the present invention to provide bis(primary phosphine) compounds for use in preparation of chiral bis(phospholane) ligands.

It is a further object of the present invention to provide a novel bis(phosphonite) compound for use in preparation of a specific bis(primary phosphine).

It is a further object of the present invention to provide either enantiomer of chiral phospholane ligands having a high degree of enantiomeric purity for use in the preparation of transition metal catalysts.

It is a further object of the present invention to provide a process for the preparation of either enantiomer of chiral phospholane ligands.

It is a further object of the present invention to provide transition metal complexes which afford high levels of stereochemical control and asymmetric induction in stoichiometric and catalytic transformations.

It is a further object of the present invention to provide a hydrogenation process using the transition metal catalysts of the present invention.

SUMMARY OF THE INVENTION

This invention comprises novel symmetrical, chiral cyclic sulfates of the formula I

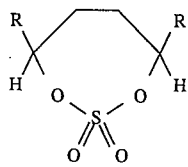

wherein:

R is a radical comprising alkyl, fluoroalkyl or perfluoroalkyl, each containing up to about 8 carbon atoms; aryl; substituted aryl; aralkyl; ring-substituted aralkyl; —CR'$_2$(CR'$_2$)qX(CR'$_2$)$_p$R';

q and p are each integers, the same or different, ranging from 1 to about 8;

X is as defined below; and

R' is H; F; aryl; or alkyl, fluoroalkyl or perfluoroalkyl, each containing up to about 8 carbon atoms;

or where together R' and R" as defined below form a ring;

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or CR'$_2$(CR'$_2$)qZ(CR'$_2$)$_p$R';

Z is O, S, NR', PR', AsR', or SbR', and

R', p, and q are as defined above;

or where together R' and R" form a ring;

provided that when R is methyl, the compound has a high degree of enantiomeric purity.

This invention further comprises a novel bis(phosphonite) compound of the following formula Va:

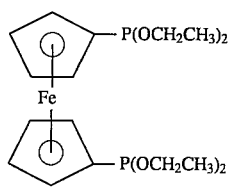

This compound is ferrocenyl-1,1'-bis(diethylphosphonite).

This invention further comprises bis(primary phosphines) of the formulae IIIb, IVb, Vb or VIb:

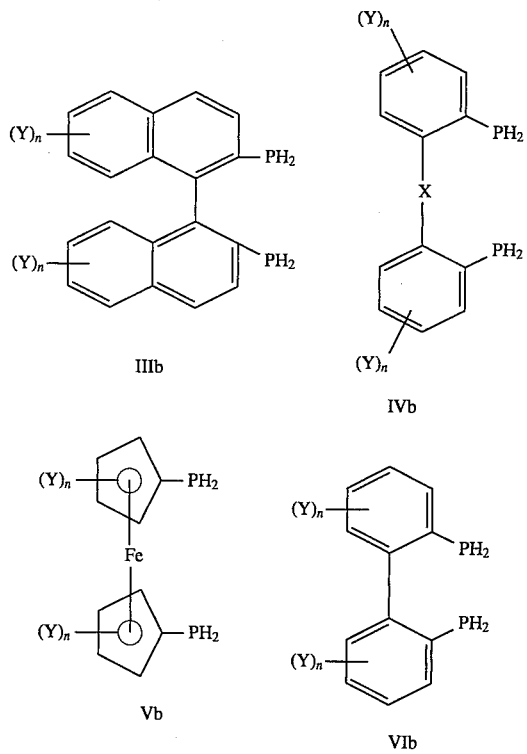

wherein:

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or CR'$_2$(CR'$_2$)qZ(CR'$_2$)$_p$R';

Z is O, S, NR', PR', AsR', or SbR', and

R' is H; F; aryl; or alkyl, fluoroalkyl or perfluoroalkyl, each containing up to about 8 carbon atoms;

q and p are each integers, the same or different, ranging from 1 to about 8;

or where together R' and R" form a ring;

and each Y is independently hydrogen, halogen, alkyl, alkoxy, aryl, aryloxy, nitro, amino, vinyl, substituted vinyl, alkynyl or sulfonic acid, and n is an integer from 1 to 6 equal to the number of unsubstituted aromatic ring carbons.

This invention further comprises novel chiral ligands of the formulae II, IIIc, IVc, Vc or VIc:

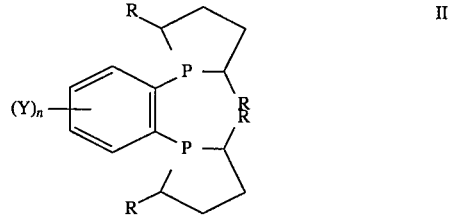

5
-continued

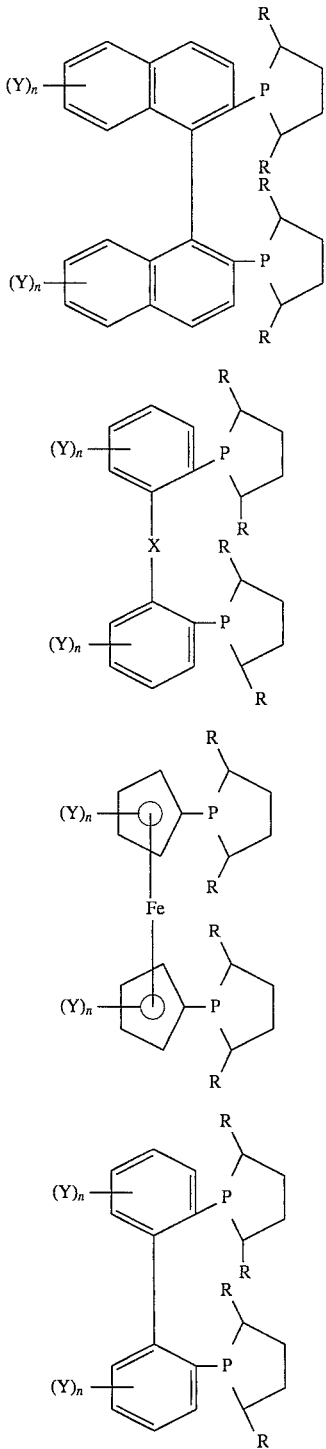

wherein:

R is a radical comprising alkyl, fluoroalkyl or perfluoroalkyl, each containing up to about 8 carbon atoms; aryl; substituted aryl; aralkyl; ring-substituted aralkyl; —CR'$_2$(CR'$_2$)$_q$X(CR'$_2$)$_p$R';

q and p are each integers, the same or different, ranging from 1 to about 8;

X is as defined below; and

R' is H; F; aryl; or alkyl, fluoroalkyl or perfluoroalkyl, each containing up to about 8 carbon atoms;

or where together R' and R" as defined below form a ring;

6

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or CR'$_2$(CR'$_2$)$_q$Z(CR'$_2$)$_p$R';

Z is O, S, NR', PR', AsR', or SbR', and

R', p, and q are as defined above;

or where together R' and R" form a ring; and each Y is independently hydrogen, halogen, alkyl, alkoxy, aryl, aryloxy, nitro, amino, vinyl, substituted vinyl, alkynyl, or sulfonic acid, and n is an integer from 1 to 6 equal to the number of unsubstituted aromatic ring carbons.

This invention further comprises a process for the preparation of chiral ligands of the above structures and others which process comprises the reaction of chiral cyclic sulfates with appropriate diphosphines in the presence of a strong base.

This invention further comprises novel chiral catalysts wherein a transition metal, lanthanide or actinide is attached to both phosphorous atoms of a chiral ligand of structure II, IIIc, IVc, Vc and VIc above.

This invention further comprises a process for the enantioselective hydrogenation of unsaturated substrates by hydrogen in the presence of novel catalysts containing chiral bis(phospholane) ligands of the structure defined as above.

DETAILED DESCRIPTION OF THE INVENTION

For the purpose of this application, by a compound "with a high degree of enantiomeric purity", or a compound "of high enantiomeric purity", is meant a compound that exhibits optical activity to the extent of greater than or equal to about 90%, preferably, greater than or equal to about 95% enantiomeric excess (abbreviated ee).

Enantiomeric excess is defined as the ratio (% R–% S)/(% R+% S), where % R is the percentage of R enantiomer and % S is the percentage of S enantiomer in a sample of optically active compound.

The present invention provides symmetric chiral 1,4-diol cyclic sulfates of formula I.

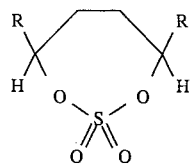

wherein:

R is a radical comprising alkyl, fluoroalkyl or perfluoroalkyl, each containing up to about 8 carbon atoms; aryl; substituted aryl; aralkyl; ring-substituted aralkyl; —CR'$_2$(CR'$_2$)$_q$X(CR'$_2$)$_p$R';

q and p are each integers, the same or different, ranging from 1 to about 8;

X is as defined below; and

R' is H; F; aryl; or alkyl, fluoroalkyl or perfluoroalkyl, each containing up to about 8 carbon atoms;

or where together R' and R" form a ring;

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or CR'$_2$(CR'$_2$)$_q$Z(CR'$_2$)$_p$R';

Z is O, S, NR', PR', AsR', or SbR', and

R', p, and q are as defined above;

or where together R' and R" form a ring;

provided that when R is methyl, the compound has a high degree of enantiomeric purity.

Preferred cyclic sulfates are those wherein R is methyl, ethyl or isopropyl.

These cyclic sulfates are prepared from 1,4-diols, and are useful in the preparation of chiral ligands having a high degree of enantiomeric purity. An example of this preparative reaction is shown in Scheme I.

Scheme I

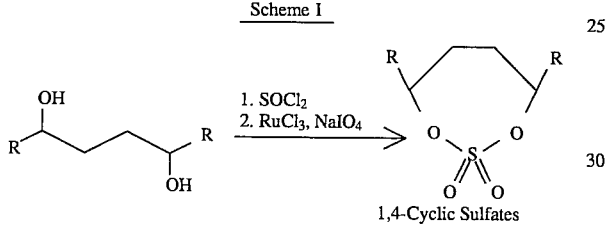

1,4-Cyclic Sulfates

I

The cyclic sulfates are prepared from readily available chiral 1,4-diols. The diols are reacted with thionyl chloride to afford the corresponding 1,4-diol cyclic sulfites (not isolated) which are subsequently oxidized to the crystalline products, symmetric 1,4-diol cyclic sulfates of formula I, by NaIO$_4$ and a catalytic amount of RuCl$_3$. The cyclic sulfates are useful in reaction with primary phosphines in the presence of strong base to prepare chiral phospholane ligands.

This invention further comprises a novel bis(phosphonite) compound of formula Va

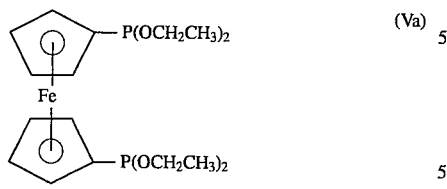

which is ferrocenyl-1,1'-bis(diethylphosphonite). It is prepared by reacting diethyl chlorophosphite with dilithioferrocene in an organic solvent such as tetrahydrofuran at a temperature of from about 20° C. to about 30° C. at ambient pressure. The compound is useful in the preparation of bis(primary phosphines).

This invention further comprises bis(primary phosphines) of the formulae IIIb, IVb, Vb, or VIb:

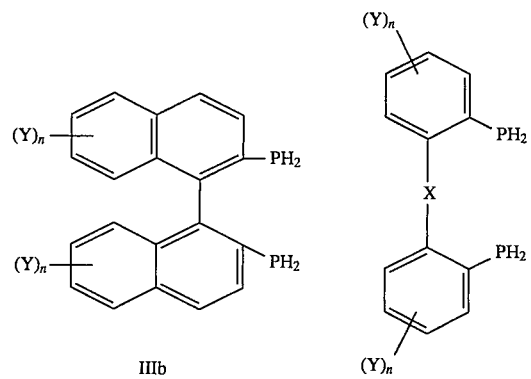

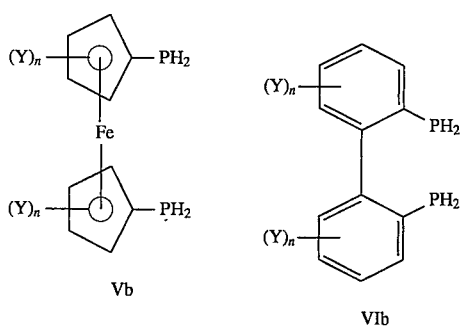

wherein:

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or CR'$_2$(CR'$_2$)$_q$Z(CR'$_2$)$_p$R';

Z is O, S, NR', PR', AsR', or SbR';

p and q are each integers, the same or different, ranging from 1 to about 8;

R' is H; F; aryl; or alkyl, fluoroalkyl or perfluoroalkyl, each containing up to about 8 carbon atoms; or where together R' and R" form a ring; and each Y is independently hydrogen, halogen, alkyl, alkoxy, aryl, aryloxy, nitro, amino, vinyl, substituted vinyl, alkynyl or sulfonic acid, and n is an integer from 1 to 6 equal to the number of unsubstituted aromatic ring carbons.

The bis(primary phosphines) of the present invention are useful as direct precursors to phosphorus-containing compounds including chiral bis(phospholane) ligands.

The outlined route to bis(phospholane) ligands involves the use of bis(primary phosphine) compounds, many of which are not available or known. The bis(primary phosphines) are prepared by treating a dimetallated aryl or alkyl compound with an excess of diethylchlorophosphite in an organic solvent, such as ether or THF, at a temperature of from about 20° C. to about 30° C. The resulting bis(diethylphosphonite) is then reacted with a mixture of lithium aluminumhydride/chlorotrimethylsilane (1/1) in the same organic solvent. Yields of bis(primary phosphine) are generally high.

A specific example is shown in Scheme II. A solution of 1,1'-dilithioferrocene (Davidson et al., *J. Organometal. Chem.*, 27, 241, 1971) in THF is reacted with diethylchlorophosphite (4 equivalents) in THF to afford the corresponding 1,1'-bis(diethylphosphonite)ferrocene in high yield (95%). This compound is subsequently reduced with 6 equivalents of a 1/1 mixture of lithium aluminumhydride and chlorotrimethylsilane (Kyba et al., Organometallics, 1, 1877, 1983) in THF solvent to provide 1,1'-diphosphinoferrocene, again in high yield (98%). Both reactions are conducted under a $N_2$ or Ar atmosphere and at a temperature of from about 20° C. to about 30° C.

Scheme II

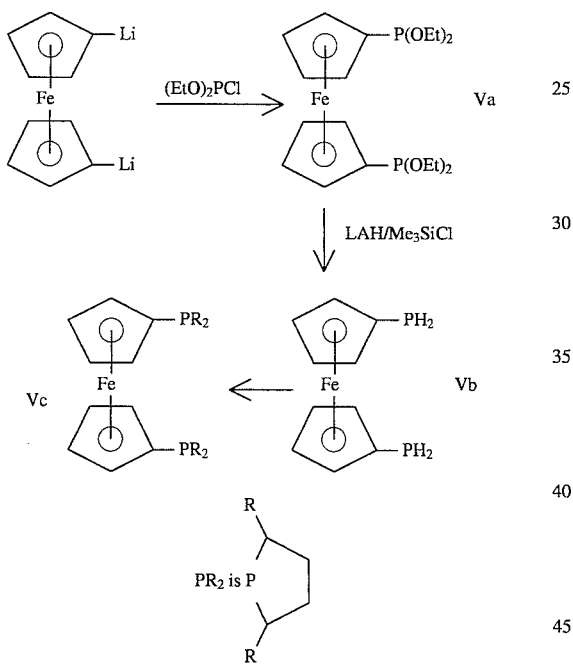

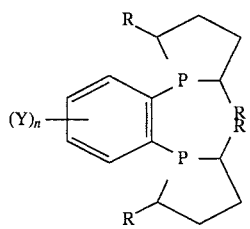

The present invention further comprises chiral bis(phospholane) ligands of formulae II, IIIc, IVc, Vc, and VIc:

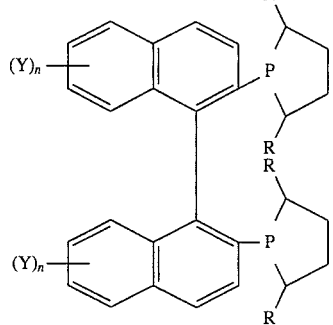  II

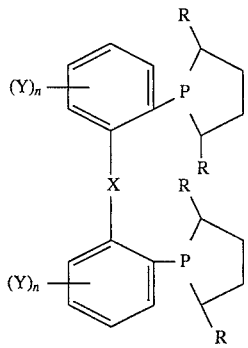  IIIc

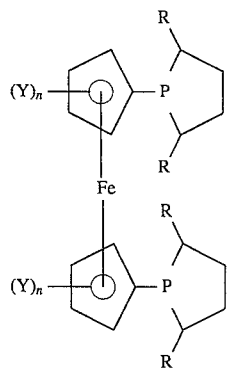  IVc

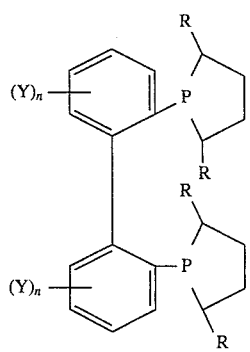  Vc

VIc wherein:
R is a radical comprising alkyl, fluoroalkyl or perfluoroalkyl, each containing up to about 8 carbon atoms; aryl; substituted aryl; aralkyl; ring-substituted aralkyl; —CR'$_2$(CR'$_2$)qX(CR'$_2$)$_p$R';

q and p are each integers, the same or different, ranging from 1 to about 8;

X is as defined below; and

R' is H; F; aryl; or alkyl, fluoroalkyl or perfluoroalkyl, each containing up to about 8 carbon atoms;

or where together R' and R" form a ring;

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or $CR'_2(CR'_2)_qZ(CR'_2)_pR'$;

Z is O, S, NR', PR', AsR', or SbR', and

R', p, and q are as defined above;

or where together R' and R" form a ring; and each Y is independently hydrogen, halogen, alkyl, alkoxy, aryl, aryloxy, nitro, amino, vinyl, substituted vinyl, alkynyl or sulfonic acid, and n is an integer from 1 to 6 equal to the number of unsubstituted aromatic ring carbons.

Preferred chiral ligands are those wherein R is methyl, ethyl, or isopropyl and Y is hydrogen. The chiral ligands of formulae II, IIIc, IVc, Vc, VIc and VII on Scheme III hereinafter are useful in the preparation of transition metal complexes which act as catalysts.

The present invention further comprises a process for the preparation of chiral ligands of structures II, IIIc, IVc, Vc, and VIc above, VII, and others, which process comprises the reaction of an appropriate diphosphine with a chiral cyclic sulfate of formula I above wherein:

R is a radical comprising alkyl, fluoroalkyl or perfluoroalkyl, each containing up to about 8 carbon atoms; aryl; substituted aryl; aralkyl; ring-substituted aralkyl; $—CR'_2(CR'_2)_qX(CR'_2)_pR'$;

q and p are each integers, the same or different, ranging from 1 to about 8;

X is as defined below; and

R' is H; F; aryl; or alkyl, fluoroalkyl or perfluoroalkyl, each containing up to about 8 carbon atoms;

or where together R' and R" form a ring;

X is O, S, NR", PR", AsR", SbR", divalent aryl, divalent fused aryl, divalent 6-membered ring heterocyclic group, divalent 5-membered ring heterocyclic group, or divalent fused heterocyclic group;

R" is hydrogen; alkyl, fluoroalkyl or perfluoroalkyl, each containing up to about 8 carbon atoms; aryl; substituted aryl; aralkyl; ring substituted aralkyl; or $CR'_2(CR'_2)_qZ(CR'_2)_pR'$;

Z is O, S, NR', PR', AsR', or SbR', and

R', p, and q are as defined above;

or where together R' and R" form a ring.

Specific examples of this process are shown in Scheme III.

Scheme III

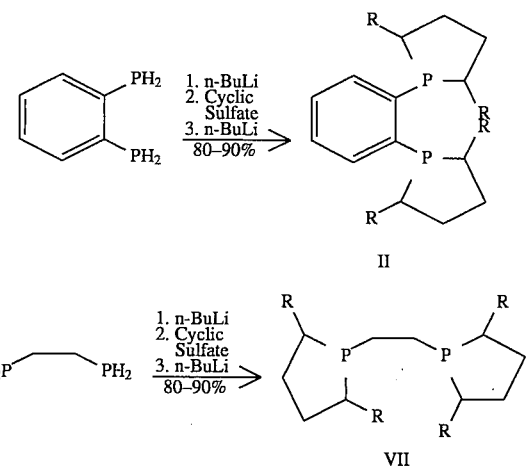

Chiral ligands are prepared by first reacting a bis(primary phosphine) or a tris(primary phosphine) with a strong base capable of deprotonating a P—H bond. Bases such as methyl lithium, n-butyl lithium, phenyl lithium, or lithium diisopropylamide, can be used to remove one proton from the phosphorus atom of each primary phosphine group, thereby creating an anion. This anion is then reacted with a cyclic sulfate of formula I to generate a carbon-phosphorus bond on each phosphorus. The addition of more strong base then removes the remaining proton from each phosphorus and subsequently creates a heterocyclic phospholane by formation of a second carbon-phosphorus bond through sulfate group displacement. The reaction is conducted in an organic solvent such as tetrahydrofuran, diethyl ether or dimethoxyethane at a temperature of from about 0° C. to the boiling point of the solvent employed. Reaction at about 20° C. to about 30° C. is preferred. An inert atmosphere is required, with nitrogen or argon being preferred. The reaction is conducted at ambient pressure.

Preferred for use in the process of the present invention are cyclic sulfates having a high degree of enantiomeric purity. Also preferred processes are those wherein R for the cyclic sulfate and resulting ligands is methyl, ethyl, or isopropyl.

More specifically, as in reaction Scheme III, deprotonation of 1,2-bis(phosphino)benzene (commercially available from Quantum Design, Inc., Austin, Tex.; 512-258-4174) in tetrahydrofuran is accomplished with n-butyllithium (2 equivalents) to give dilithium 1,2-bis(phosphido)benzene. The resulting dianion is then reacted with a tetrahydrofuran solution of 1, 4-diol cyclic sulfate of formula I (2 equivalents), followed after 1 hour, by the second addition of n-butyl lithium (2.2 to 2.3 equivalents). Standard workup procedures afford the pure products, 1,2-bis(phospholano)benzenes exemplified by formula II, in good yield (80–90%). In general, the crude products obtained through this procedure are analytically pure and no further purification steps (ie. distillation) are required.

By using the commercially available 1,2-bis(phosphino)ethane (Quantum Design, Inc., Austin, Tex.; 512-258-4174), the bis(phospholano)ethanes of formula VII, previously described in U.S. Pat. No. 5,008,457, also are readily prepared in high yield and in pure form by this route (Scheme III). The described synthesis appears only to be limited by the availability of the primary phosphine starting material, and can be easily applied to the preparation of other chiral ligands such as those of formulae IIIc, IVc, Vc or VIc. Other phosphines of current interest are 1,1'-bis-(phospholano)ferrocene of formula Vb and 2,2'-bis(phospholano)binaphthyl of formula IIIb, both of which are accessible through this synthetic route.

The great advantages of this new synthetic approach to chiral phospholanes are the experimental simplicity, high yields and product purity (essentially enantiomerically pure products are obtained and no P—P dimer or phosphine diastereomers are ever observed), and its amenability to increasing the scale of the preparation. Various bis(phospholanes) previously difficult to prepare can be readily synthesized by this route.

The present invention further comprises complexes wherein a transition metal, lanthanide or actinide, is attached to both phosphorus atoms of the chiral ligands of formulae II, IIIc, IVc, Vc, VIc or VII as defined above. Such complexes are prepared by reacting the chiral ligand with an appropriate precursor complex. Typical precursor transition metal complexes suitable for use herein include, among others, $[(COD)_2Rh]^+X^-$ wherein COD is 1,5-cyclooctadiene, and X is $BF_4$, $SbF_6$, $PF_6$, $CF_3SO_3$; or $[CODRu(2-methylallyl)_2]$ wherein COD is as previously defined. The preparation is usually conducted in an organic solvent under an inert atmosphere such as nitrogen or argon. The reaction is conducted at ambient pressure at a temperature between 0° C. and the boiling point of the solvent. The resulting complexes containing the bis(phospholanes) have a high degree of enantiomeric purity and are useful as catalysts which provide high enantiomeric selectivity in hydrogenation of unsaturated substrates.

A further aspect of the present invention comprises an improved process for hydrogenation of unsaturated substrates wherein the improvement comprises using the complexes as described above as catalysts. Suitable unsaturated substrates include acetamidoacrylates, enol acetates such as 1-acetoxy-(substituted aryl)ethylenes, itaconate esters, ketones, olefins, substituted olefins, imines, enol carbamates, and α,β-unsaturated carboxylic acids. Generally a reactor is charged with substrate and catalyst and optionally with solvent and pressurized with hydrogen gas. Hydrogenation can be carried out in a batch or in a continuous manner. Hydrogen uptake is monitored. Reaction completion is monitored by gas chromatography or nuclear magnetic resonance.

Several rhodium and ruthenium complexes containing the new chiral phospholane ligands of the present invention have been prepared and were shown to provide very high levels of asymmetric induction in hydrogenation reactions yielding hydrogenated products having a high degree of enantiomeric purity. For example, enantiomeric excesses approaching 100% ee were observed in the hydrogenation of methyl acetamidocinnamate, dimethyl itaconate, methyl acetamidoacrylate and 2-methyl-2-butenoic acid. The rates and catalytic efficiencies (0.1 mol % catalyst) of these reactions were extremely high.

The following examples illustrate the present invention, but are not intended to limit it in any manner.

It is understood that the following procedures can be used to generate either enantiomer of the chiral compounds listed in a high degree of enantiomeric purity.

General Procedures

All reactions and manipulations were performed in a nitrogen-filled Vacuum Atmospheres Dri-Lab glovebox or using standard Schlenk-type techniques. Benzene, toluene, diethyl ether ($Et_2O$), tetrahydrofuran (THF), glyme, hexane, and pentane were distilled from sodiumbenzophenone ketyl under nitrogen. Acetonitrile ($CH_3CN$) and methylene chloride ($CH_2Cl_2$) were distilled from $CaH_2$. Methanol (MeOH) was distilled from $Mg(OMe)_2$.

Melting points were determined using a Mel-Temp apparatus in capillaries sealed under nitrogen and are uncorrected. HPLC analyses were performed using a Hewlett Packard Model HP 1090 LC interfaced to a HP 9000 Series 300 computer workstation. Optical Rotations were obtained using a Perkin Elmer Model 241 MC Polarimeter. NMR spectra were obtained on Nicolet NT-360 wide-bore (360 MHz $^1$H 146 MHz $^{31}$P), Nicolet NMC-300 wide-bore (300 MHz $^1$H, 120.5 MHz $^{31}$P, 75.5 Mz $^{13}$C) and Nicolet QM-300 narrow-bore (300 MHz $^1$H) spectrometers. $^{13}$C and $^{31}$P NMR chemical shifts are positive downfield (and negative upfield) from external $Me_4Si$ and 85% $H_3PO_4$, respectively. IR spectra were recorded on a Nicolet 5DXB FT-IR spectrometer. Elemental analyses were performed by Oneida Research Services, Inc., Whitesboro, N.Y., Schwarzkopf Microanalytical Laboratory, Inc., Woodside, N.Y., or Pascher Mikroanalytisches Labor, Remagen-Bandorf (FRG).

EXAMPLE 1 a) Chiral β-hydroxy esters

The preparation of chiral β-hydroxy esters used in the diol syntheses was carried out as described by Noyori et al., J. Amer. Chem. Soc., 109, 5856 (1987) which is herein incorporated by reference who have reported the asymmetric reduction of β-keto esters using a ruthenium catalyst bearing the chiral phosphine ligand BINAP (both enantiomers commercially available from Strem Chemicals). All keto ester reductions were conducted on a 300 g scale in Hasteloy steel autoclave vessels in a $MeOH/CH_2Cl_2$ (300 mL/300 mL) solvent mixture. The reactions were allowed to proceed at constant $H_2$ pressure (1500 psi) for 48 h at 25° C. Complete conversion of the β-keto ester substrates was observed in all cases and the products were simply distilled from the crude reaction mixture. Consistent with the results of Noyori et al., all products were determined >99% enantiomerically pure.

b) Chiral β-hydroxy acids

A mixture of (3R)-methyl 3-hydroxypentanoate (290 g, 2.2 mol) in water (200 mL) and ethanol (200 mL) was cooled to 0° C. To this cold solution was added a solution of KOH (185 g, 3.3 mol) in water (1 L). The reaction was then allowed to stir at 25° C. for 48 h. The resulting solution was concentrated to ca. 500 mL and acidified (conc. HCl) until pH=1 was reached. The precipitated salts were filtered and the filtrate was subjected to continuous liquid/liquid extraction with diethyl ether (1 L) for 24 h. The diethyl ether was removed on a rotovap to afford the product β-hydroxy acid as a colorless oil (250 g, 97%). The crude product was sufficiently pure to use in the next step (Kolbe-coupling).

c) (2R,5R)-2,5-hexanediol

A 1000 mL jacketed reaction vessel was charged with (3R)-3-hydroxybutyric acid (52.0 g, 0.5 mol), methanol (390 mL) and sodium methoxide (110 mL of a 0.5N solution in methanol, 0.055 mol), and the mixture (pH=5.38) was cooled to 0° C. with a circulating bath. The electrode configuration used consists of a Pt foil anode (20 cm$^2$) wrapped around the outside bottom of a small jointed tube which fit inside a larger jointed tube with a Pt foil cathode (30 cm$^2$) lining the inside (avg electrode gap=2.5 mm). Using a 30 amp DC power supply (Hewlett Packard Model No. 6269B), a constant current (current density 0.25 A/cm$^2$) of 5 amp was applied until 56,000 coulombs (1.2 F/mol)

were passed at which point complete conversion of hydroxy acid was indicated by gas chromatography. The reaction and gas evolution ($H_2$ and $CO_2$) proceed normally until ca. 1.0 F/mol current were passed, after which the resistance and solution pH are observed to increase. The colorless reaction mixture was then concentrated on a rotovap, and the resulting solid residue was extracted EtOAc (500 mL). After filtering, the remaining solids were stirred with EtOAc (100 mL) for 10 h, filtered, and the combined EtOAc extracts (600 mL) were concentrated to a colorless solid. The solids were dissolved in a minimum amount of warm $Et_2O$, quickly filtered through a coarse frit, and the filtrate cooled to $-78°$ C. After two hours, the colorless crystals were filtered, washed with cold pentane, and dried in vacuo (Yield 14.4 g, 48%). mp 53°–54° C.; $[\alpha]^{25}{}_D=-39.6°\pm0.50°$ (c 1, $CHCl_3$) $^1H$ NMR ($CD_2Cl_2$) $\delta 1.15$ (d, $J_{HH}=6.2$ Hz, 6H, $CH_3$), 1.50 (m, 4H, $CH_2$), 2.95 (br, 2H, OH), 3.75 (m, 2H, CH); $^{13}C$ NMR ($CD_2Cl_2$) d 23.6, 35.9, 68.1. Anal. Calcd for $C_6H_{14}O_2$: C, 60.98; H, 11.94. Found: C, 61.12; H, 11.64.

d) (2S,5S) -2,5-hexanediol

This compound was prepared as described in c) above except that (3S)-3-hydroxybutyric acid was used as substrate. $[\alpha]^{25}{}_D=+39.4°\pm0.5°$ (c 1, $CHCl_3$). Other spectroscopic properties were identical to those given for the product of c) above.

e) 2R,5R)-2,5-hexanediol cyclic sulfate

To (2R,5R)-2,5-hexanediol of Example 1c) (10.0 g, 0.085 mol) in $CCl_4$ (60 mL) was added via syringe thionyl chloride (7.75 mL, 0.106 mol). The resulting brownish solution was then refluxed for 1.5 hour. After cooling to 25° C. the reaction was concentrated on a rotovap to afford a brown oil. The oil Was then dissolved in a mixture of $CCl_4$ (60 mL), $CH_3CN$ (60 mL), and $H_2O$ (90 mL) and the mixture was cooled to 0° C. To the cool mixture was added $RuCl_3$ trihydrate (0.12 g, 0.58 mmol) followed by solid $NaIO_4$ (36.2 g, 0.169 mol). The reaction was allowed to stir at 25° C. for 1 h. At this point, $H_2O$ (400 mL) was added and the mixture was extracted with diethyl ether (4×200 mL) and the combined ether extracts were washed with brine (2×100 mL). After drying over $MgSO_4$ and filtration through a pad of $SiO_2$ (important to remove dissolved Ru salts), the colorless solution was concentrated to ca. 20 mL on a rotovap. The addition of hexane (70 mL) and cooling to $-10°$ C. afforded the product as a colorless crystalline solid which was filtered, washed with cold hexane and dried. Recrystallization from ether/hexane in a similar manner yielded pure colorless crystalline product of the title which is best stored below 0° C. (12.4 g, 81%): mp 80° C. (dec.); $[\alpha]^{25}{}_D=-32.4°$ (c1. $CHCl_3$); $^1H$ NMR ($CDCl_3$) $\delta 1.32$ (d, $J_{HH}=6.5$ Hz, 6H, $CH_3$), 1.55 (m, 2H, $CH_2$), 2.20 (m, 2H, $CH_2$), 3.60 (m, 2H, CH); $^{13}C$ NMR ($CDCl_3$) $\delta 22.67$, 39.53, 44.31; HRMS (EI, direct insert): m/z 181.0551 ($M^++H$, exact mass calcd for $C_6H_{13}O_4S$: 181.0534), 137.0284 ($M-C_2H_3O$).

EXAMPLE 2

(3S,6S)-3,6-octanediol cyclic sulfate

To (3S,6S)-3,6-octanediol prepared as in Example 1d) (15.0 g, 0.103 mol) in $CCl_4$ (60 mL) was added via syringe thionyl chloride (9.4 mL, 0.128 mol). The resulting brownish solution was then refluxed for 1.5 h. After cooling to 25° C., the reaction was concentrated on a rotovap to afford a brown oil. The oil was then dissolved in a mixture of $CCl_4$ (90 mL), $CH_3CN$ (90 mL), and $H_2O$ (135 mL) and the mixture was cooled to 0° C. To the cool mixture was added $RuCl_3$ trihydrate (0.18 g, 0.87 mmol) followed by solid $NaIO_4$ (44.06 g, 0.206 mol). The reaction was allowed to stir at 25° C. for 1 h. At this point, $H_2O$ (500 mL) was added and the mixture was extracted with diethyl ether (4×200 mL) and the combined ether extracts were washed with brine (2×100 mL). After drying over $MgSO_4$ and filtration through a pad of $SiO_2$ (important to remove dissolved Ru salts), the colorless solution was concentrated to ca. 20 mL on a rotovap. The addition of hexane (70 mL) and cooling to $-10°$ C. afforded the titled product as a colorless crystalline solid which was filtered, washed with cold hexane and dried. Recrystallization from ether/hexane in a similar manner yielded pure colorless crystalline product (15.1 g, 71%): mp 79.5°–80.5° C.; $[\alpha]^{25}{}_D=+28.6°$ (c1. $CHCl_3$); $^1H$ NMR ($CDCl_3$) $\delta 0.98$ (t, $J_{HH}=7.2$ Hz, 6H, $CH_3$), 1.5–1.75 (m, 6H, $CH_2$), 2.20 (m, 2H, $CH_2$), 3.35 (m, 2H, CH); $^{13}C$ NMR ($CDCl_3$) $\delta 13.15$, 30.62, 36.89, 51.34.

EXAMPLE 3

(3S,6S)-3,6-dihydroxy-2,7-dimethyloctane cyclic sulfate

To (3S,6S)-3,6-dihydroxy-2,7-dimethyloctane prepared as in Example 1d) (14.75 g, 0.085 mol) in $CCl_4$ (60 mL) was added via syringe thionyl chloride (7.75 mL, 0.106 mol). The resulting pale yellow solution was then refluxed for 1.5 h. After cooling to 25° C., the reaction was concentrated on a rotovap to afford a pale yellow oil. The oil was then dissolved in a mixture of $CCl_4$ (60 mL), $CH_3CN$ (60 mL), and $H_2O$ (90 mL) and the mixture was cooled to 0° C. To the cool mixture was added $RuCl_3$ trihydrate (0.12 g, 0.58 mmol) followed by solid $NaIO_4$ (36.2 g, 0.169 mol). The reaction was allowed to stir at 25° C. for 1 h. At this point, $H_2O$ (400 mL) was added and the mixture was extracted with diethyl ether (4×200 mL) and the combined ether extracts were washed with brine (2×100 mL). After drying over $MgSO_4$ and filtration through a pad of $SiO_2$ (important to remove dissolved Ru salts), the colorless solution was concentrated to dryness on a rotovap to afford a colorless crystalline material. Recrystallization from warm hexane (25 mL) and cooling to $-10°$ C. afforded the titled product as a colorless crystalline solid which was filtered, washed with cold hexane and dried (18.14 g, 90%): mp 92.5°–93.5° C.; $[\alpha]^{25}{}_D=-55.0°$ (c1. $CHCl_3$); $^1$NMR ($CDCl_3$) $\delta 0.97$ (d, $J_{HH}=6.72$ Hz, 6H, $CH_3$), 0.98 (d, $J_{HH}=6.66$ Hz, 6H, $CH_3$), 1.85 (m, 2H, CH), 1.90 (m, 4H, $CH_2$), 4.40 (m, 2H, CH); $^{13}C$ NMR ($CDCl_3$) $\delta 17.11$, 18.67, 30.01, 32.79, 89.50.

EXAMPLE 4

1,2-Bis((2S,5S)-2,5-dimethylphospholano)benzene

To 1,2-bis(phosphino)benzene (0.79 g, 5.56 mmol) in THF (100 mL) was added dropwise via syringe n-BuLi (6.95 mL of a 1.6M solution in hexane, 2.0 equiv.). The yellow solution was allowed to stir for 1.5 h during which it became slightly cloudy. To the resulting mixture was then added a THF solution (10 mL) of (2R,5R)-2,5-hexanediol cyclic sulfate prepared as in Example 1e) (2.03 g, 11.3 mmol) upon which the reaction decolorized. After stirring for 1 h, n-BuLi (7.65 mL of a 1.6M hexane solution, 2.2 equiv.) was again added dropwise via syringe. Initially, a yellow color appeared and then faded, and a gelatinous precipitate formed (additional THF may be added at this point in order to maintain stirring). Toward the end of the addition the reaction remained yellow. The mixture was allowed to stir for 1.5 h, after which MeOH (3 mL) was added to quench any excess n-BuLi remaining. The resulting colorless mixture was filtered, and the gelatinous precipitate was washed thoroughly with diethyl ether. The filtrate was concentrated to produce a solid residue which was extracted with pentane (50 mL) and filtered. Concentration of the filtrate to 10 mL and cooling to −10° C. led to the titled product as colorless crystals (0.80 g) which were filtered and dried in vacuo. Further concentration of the filtrate and recrystallization of the residue from MeOH at −10° C. led to a second crop of crystals (0.53 g) which were filtered and dried in vacuo. Combined total yield 1.33 g (78%): $[\alpha]_D^{25}=+476°$ (c1, hexane); $^1$H NMR ($C_6D_6$) $\delta$0.95 (ddd, 6H, $CH_3$), 1.24 (ddd, 6H, $CH_3$), 1.20–1.35 (m, 2H, $CH_2$), 1.70 (m, 1H, $CH_2$), 1.95 (m, 1H, $CH_2$), 2.45 (m, 2H, CH), 7.05 (m, 2H, Ph), 7.25 (m, 2H, Ph); $^{31}$P NMR ($C_6D_6$) $\delta$+2.9; $^{13}$C NMR ($C_6D_6$) $\delta$18.65, 20.66 (t, $J_{CP}$=18.2 Hz, $CH_3$), 32.89, 34.38 (t, $J_{CP}$=6.8 Hz), 35.91, 36.49, 128.0, 131.49, 144.56; HRMS (EI, direct insert): m/z 306.1638 ($M^+$, exact mass calcd for $C_{18}H_{28}P_2$: 306.1667), 223.0796 ($M-C_6H_{11}$), 192.1064 ($M-C_6H_{11}P$).

EXAMPLE 5

1,2-Bis((2R,5R)-2,5-diethylphospholano)benzene

To 1,2-bis(phosphino)benzene (1.01 g, 7.11 mmol) in THF (100 mL) was added dropwise via syringe n-BuLi (8.90 mL of a 1.6M solution in hexane, 2.0 equiv.). The yellow solution was allowed to stir for 1.5 h during which it became slightly cloudy. To the resulting mixture was then added a THF solution (10 mL) of (3S,6S)-3,6-octanediol cyclic sulfate prepared as in Example 2 (3.0 g, 14.4 mmol) upon which the reaction decolorized. After stirring for 1 h, n-BuLi (9.80 mL of a 1.6M hexane solution, 2.2 equiv.) was again added dropwise via syringe. Initially, a yellow color appeared and then faded. Toward the end of the addition the reaction remained yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the titled product as a colorless oil (2.02 g, 78%). The crude product was essentially pure and could be used without any further purification. If further purification is desired, the product may be distilled in vacuo: $[\alpha]_D^{25}=-265°$ (c1, hexane); $^1$H NMR ($C_6D_6$) $\delta$0.85 (m, 6H, $CH_3$), 0.80–0.90 (m, 2H, $CH_2$), 0.97 (t, $J_{HH}$=7.3 Hz, 6H, $CH_3$), 1.10–1.40 (m, 4H, $CH_2$), 1.50–1.80 (m, 6H, $CH_2$), 1.90 (m, 2H, CH), 2.00–2.20 (m, 4H, $CH_2$), 2.35 (m, 2H, CH), 7.06 (m, 2H, Ph), 7.31 (m, 2H, Ph); $^{31}$P MMR ($C_6D_6$) $\delta$−4.5; $^{13}$C NMR ($C_6D_6$) $\delta$13.99, 14.11 (d, $J_{PC}$=4.15 Hz), 25.37, 28.80 (t, $J_{PC}$=16.56 Hz), 33.06, 33.37, 41.92, 42.34 (t, $J_{CP}$=6.70 Hz), 127.62, 132.25, 144.33; HRMS (EI, direct insert): m/z 362.2245 ($M^+$, exact mass calcd for $C_{22}H_{36}P_2$: 362.2292 ), 293.1570 ($M-C_5H_9$), 251.1086 ($M-C_8H_{15}$), 216.1193 ($M-C_{11}H_{14}$), 185.1395 ($M-C_{11}H_{14}P$).

EXAMPLE 6

1,2-Bis((2R,5R)-2,5-diethylphosopholano)ethane

To 1,2-bis(phosphino)ethane (0.667 g, 7.10 mmol) in THF (100 mL) was added via syringe n-BuLi (8.90 mL of a 1.6M solution in hexane, 2.0 equiv.). The pale yellow solution was allowed to stir for 1.5 h. To the resulting mixture was then added a THF solution (10 mL) of (3S, 6S)-3,6-octanediol cyclic sulfate prepared as in Example 2 (3.0 g, 14.4 mmol) upon which the reaction decolorized. After stirring for 1 h, n-BuLi (10.2 mL of a 1.6M hexane solution, 2.3 equiv.) was again added dropwise via syringe. Initially, a yellow color appeared and then faded, and a gelatinous precipitate formed (additional THF may be added at this point in order to maintain stirring). Toward the end of the addition the reaction remained pale yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the titled product as a colorless oil (1.92 g, 86%). The crude product was essentially pure and could be used without any further purification. If further purification is desired, the product may be distilled in vacuo: $[\alpha]_D^{25}=+320°$ (c1, hexane); $^1$H NMR ($C_6D_6$) $\delta$0.93 (t, $J_{HH}$=8.2 Hz, 6H, $CH_3$), 0.95–1.10 (m, 2H, $CH_2$), 1.03 (t, $J_{HH}$=7.8 Hz, 6H, $CH_3$), 1.15–1.40 (m, 6H, $CH_2$), 1.45–1.75 (m, 12H, $CH_2$), 1.80 (m, 2H, CH), 1.95 (m, 2H, CH); $^{31}$P NMR ($C_6D_6$) $\delta$−5.9; $^{13}$C NMR ($C_6D_6$) $\delta$14.75, 15.00, 20.32, 23.48, 29.46, 34.13, 34.94, 43.08, 45.85; HRMS (EI, direct insert): m/z 314.2289 ($M^+$, exact mass calcd for $C_{18}H_{36}P_2$: 314.2292), 286.1949 ($M-C_2H_4$), 203.1099 (M-C8H15), 172.1372 ($M-C_8H_{15}P$), 144.1037 ($C_8H_{17}P$ fragment).

EXAMPLE 7

1,2-Bis((2R,5R)-2,5-diisopropylpholano)ethane

To 1,2-bis(phosphino)ethane (0.50 g, 5.32 mmol) in THF (75 mL) was added via syringe n-BuLi (6.65 mL of a 1.6M solution in hexane, 2.0 equiv.). The pale yellow solution was allowed to stir for 1.5 h. To the resulting mixture then was added a THF solution (10 mL) of (3S,6S)-3,6-dihydroxy-2, 7-dimethyloctane cyclic sulfate prepared as in Example 3 (2.53 g, 10.7 mmol) upon which the reaction decolorized. After stirring for 1 h, n-BuLi (7.64 mL of a 1.6M hexane solution, 2.3 equiv.) was again added dropwise via syringe. Initially, a yellow color appeared and then faded, and a gelatinous precipitate formed (additional THF may be added at this point in order to maintain stirring). Toward the end of the addition the reaction remained pale yellow. The mixture was allowed to stir for 1.5 h, after which MeOH (3 mL) was added to quench any excess n-BuLi remaining. The resulting colorless mixture was concentrated to produce a gelatinous residue which was extracted with pentane (ca. 150 mL) and filtered. Concentration of the filtrate to ca. 10 mL and cooling to −20° C. provided the titled product as colorless crystals which were filtered and dried in vacuo (1.45 g, 74%). The crude product was analytically pure and could be used without any further purification. If further purification is desired, the product may be recrystallized from $Et_2O$/MeOH at −20° C. to provide colorless crystals: $[\alpha]_D^{25}=-264°\pm3°$ (c 1, hexane); $^1$H NMR ($C_6D_6$) $\delta$0.84 (d, $J_{HH}$=6.4 Hz, 6H, $CH_3$), 0.80–1.10 (m, 2H, $CH_2$), 0.95 (d, $J_{HH}$=6.6 Hz, 6H, $CH_3$), 1.09 (d, $J_{HH}$=6.5 Hz, 6H, $CH_3$), 1.10 (d, $J_{HH}$=6.5 Hz, 6H, $CH_3$), 1.20–1.45 (m, 4H, $CH_2$), 1.45–1.75 (m, 8H, CH, $CH_2$), 1.80–2.05 (m, 4H, CH); $^{31}$P NMR ($C_6D_6$) $\delta$−10.1; $^{13}$C NMR ($C_6D_6$) $\delta$20.27, 20.36, 22.24, 22.81, 23.21, 24.52, 29.48, 32.84, 33.04, 50.32, 52.19; HRMS (EI, direct insert): m/z 370.2894 ($M^+$, exact mass calcd for $C_{22}H_{44}P_2$: 370.2918), 355.2603 ($M-CH_3$), 342.2634 ($M-C_2H_4$), 327.2336 ($M-C_3H_7$), 231.1241 ($M-C_{10}H_{19}$), 199.1611 ($M-C_{10}H_{20}P$ fragment), 172.1387 ($C_{12}H_{23}P$ fragment).

EXAMPLE 8

1,2-Bis((2R,5R)-2,5-diisopropylphospholano)benzene

To 1,2-bis(phosphino)benzene (1.20 g, 8.44 mmol) in THF (100 mL) was added dropwise via syringe n-BuLi (10.6 mL of a 1.6M solution in hexane, 2.0 equiv.). The yellow solution was allowed to stir for 1.5 h during which it became slightly cloudy. To the resulting mixture was then added a THF solution (10 mL) of (3S,6S)-3,6-dihydroxy-2,7-dimethyloctane cyclic sulfate prepared as in Example 3 (4.01 g, 17.0 mmol) upon which the reaction decolorized. After stirring for 1 h, n-BuLi (12.15 mL of a 1.6M hexane solution, 2.2 equiv.) was again added dropwise via syringe. Initially, a yellow color appeared and then faded. Toward the end of the addition the reaction remained yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the titled product as a viscous colorless oil (2.47 g, 70%). The crude product was essentially pure and could be used without any further purification. Further purification, if desired, may be accomplished by distillation in vacuo: $[\alpha]_D^{25}$+59.6°±1° (c1, hexane); $^1$H NMR (C$_6$D$_6$) δ0.65 (d, $J_{HH}$=6.4 Hz, 6H, CH$_3$), 0.80–1.10 (m, 2H, CH$_2$), 1.03 (d, $J_{HH}$=6.6 Hz, 12H, CH$_3$), 1.10 (d, $J_{HH}$=6.5 Hz, 6H, CH$_3$), 1.20–1.65 (m, 6H, CH$_2$), 1.65–2.20 (m, 6H, CH, CH$_2$), 2.40 (m, 2H, CH), 7.00 (m, 2H, Ph), 7.40 (m, 2H, Ph); $^{31}$P NMR (C$_6$D$_6$) δ–11.2; HRMS (EI, direct insert): m/z 418.2916 (M$^+$, exact mass calcd for C$_{26}$H$_{44}$P$_2$: 418.2918), 403.2633 (M-CH$_3$), 375.2351 (M-C$_3$H$_7$), 279.1535 (M-C$_{10}$H$_{19}$), 247.1485 (M-C$_{10}$H$_{20}$P fragment).

EXAMPLE 9

Ferrocenyl-1,1'-bis(diethylphosphonite)

To diethyl chlorophosphite (8.0 g, 0.051 mol) in THF (15 mL) was added dropwise a THF solution of 1,1'-dilithioferrocene (4.0 g, 0.013 mol). The reaction was allowed to stir for 2 h at 25° C. after which $^{31}$P NMR monitoring indicated complete conversion to product. The reaction was then concentrated in vacuo, and the resulting orange residue was extracted with pentane. After filtering through a pad of celite, the filtrate was concentrated to give the product as a dark orange oil (5.15 g, 95%): $^1$H NMR (C$_6$D$_6$) δ1.05 (t, 3H, CH$_3$), 3.75 (d, 2H, CH$_2$), 4.25 (s (br), 2H, CpH), 4.45 (s (br), 2H, CpH); $^{31}$P NMR (C$_6$D$_6$) δ156.5.

EXAMPLE 10

1,1'-Bis(phosphino)ferrocene

To a cold (–30° C.) solution of lithium aluminumhydride (1.07 g, 28.2 mmol) in THF (75 mL) is added a cold solution (–30° C.) of chlorotrimethylsilane (3.06 g, 28.2 mmol) in THF (5 mL), and the mixture is allowed to stir at 25° C. for 1.5 h. To the resulting mixture is added a solution of compound prepared in Example 9, ferrocenyl-1,1'-bis(diethylphosphonite) (2.0 g, 4.7 mmol), in THF (10 mL). The reaction was allowed to stir at 25° C. for 6 h, after which a solution of MeOH (5 mL) in THF (10 mL) was slowly added dropwise. After stirring for 1 h, the reaction was filtered and the filtrate concentrated to dryness. The residue was extracted with diethyl ether (100 mL), filtered, and concentrated to an orange oil. The resulting oil was dissolved in pentane, filtered, and the filtrate concentrated to afford the product as an orange oil (1.15 g, 98%): $^1$H NMR (C$_6$D$_6$) δ3.36 (t, $J_{PH}$=202 Hz, $J_{HH}$=3.3 Hz, 2H, PH), 3.92 (m, 2H, CpH), 3.96 (m, 2H, CpH), 4.03 (t, $J_{PH}$=202 Hz, $J_{HH}$=3.3 Hz, 2H, PH); $^{31}$P NMR (C$_6$D$_6$) δ–145.5 (t, $J_{PH}$=202 Hz); $^{13}$C NMR (C$_6$D$_6$) δ72.14, 76.99, 77.0 (d, $J_{PC}$=15.2 Hz).

EXAMPLE 11

1,1'-Bis((2R,5R)-2,5-diethylphospholano)ferrocene

To a solution of 1,1'-bis(phosphino)ferrocene (0.2 g, 0.8 mmol) in THF (30 mL) was added dropwise via syringe n-BuLi (1.0 mL of a 1.6M solution in hexane, 2.0 equiv.). The orange solution was allowed to stir for 1.5 h during which it became slightly cloudy. To the resulting mixture was then added a THF solution (10 mL) of (3S,6S)-3,6-octanediol cyclic sulfate (0.338 g, 1.6 mmol). After stirring for 1 h, n-BuLi (1.15 mL of a 1.6M hexane solution, 2.2 equiv.) was again added dropwise via syringe. The mixture was allowed to stir for 1.5 h, after which MeOH (3 mL) was added to quench any excess n-BuLi remaining. The resulting orange mixture was concentrated to produce a gelatinous residue which was extracted with pentane (150 mL) and filtered. Concentration of the filtrate to 5 mL and cooling to –30° C. for 10 h afforded the product as an orange crystalline solid which was filtered, washed with cold MeOH and dried (0.29 g, 77%). The crude product was essentially pure and may be used without any further purification. $^1$H NMR (C$_6$D$_6$) δ0.88 (m, 6H, CH$_3$), 0.9–1.20 (m, 4H, CH$_2$), 1.11 (t, $J_{HH}$=7.3 Hz, 6H, CH$_3$), 1.20–1.40 (m, 4H, CH$_2$), 1.45–1.70 (m, 4H, CH$_2$), 1.70–1.90 (m, 4H, CH), 2.10 (m (br), 2H, CH$_2$), 2.40 (m, 2H, CH), 3.90 (m, 1H, CpH), 4.25 (m, 2H, CpH), 4.35 (m, 1H, CpH); $^{31}$P NMR (C$_6$D$_6$) δ–9.4; $^{13}$C NMR (C$_6$D$_6$) δ14.27 (d, $J_{PC}$=16.1 Hz), 14.82 (d, $J_{PC}$=7.9 Hz), 23.76, 30.07, 30.49, 34.03, 34.34 (d, $J_{PC}$=4.4 Hz), 42.42 (d, $J_{CP}$=9.9 Hz), 44.44 (d, $J_{CP}$=11.9 Hz), 70.88 (d, $J_{CP}$=6.2 Hz), 71.24, 71.96 (d, $J_{CP}$=7.7 Hz), 77.33 (d, $J_{CP}$=32.8 Hz); HRMS (EI, direct insert): m/z 470.1976 (M$^+$, exact mass calcd for C$_{26}$H$_{40}$P$_2$Fe: 470.1955), 359.0485 (M-C$_8$H$_{15}$), 328.1046 (M-C$_8$H$_{15}$P).

EXAMPLE 12

Ruthenium complex [(2-methylallyl)$_2$Ru-(1,2-Bis((2S,5S)-2,5-dimethylphospholano)benzene)]

To [(COD)Ru(2-methylallyl)$_2$] (0.104 g, 0.325 mmol) in hexane (10 mL) was added 1,2-bis((2S,5S)-2,5-dimethylphospholano)benzene prepared as in Example 4 in hexane (3 mL) and the mixture was refluxed for 12 h. After cooling, the reaction was concentrated to dryness and the residue dissolved in a minimum amount of diethyl ether (2–3 mL). The addition of MeOH (10 mL) and cooling to –30° C. afforded the product as an off-white solid which was filtered, washed with cold MeOH, and dried in vacuo (0.124 g, 74%). $^1$H NMR (C$_6$D$_6$) δ0.35 (dd, $J_{HH}$=6.9 Hz, $J_{PH}$=9.7 Hz, 6H, CH$_3$), 0.70 (d, 2H), 1.20 (m, 2H) 1.30–1.50 (m, 6H, CH$_2$), 1.40 (dd, $J_{HH}$=7.4 Hz, $J_{PH}$=17.2 Hz, 6H, CH$_3$), 1.65 (s, 2H, CH), 1.5–2.0 (m, 4H), 2.20 (s, 6H, CH$_3$), 2.65 (m, 2H, CH, CH$_2$), 2.75 (s, 2H, CH), 7.05 (m, 2H, Ph), 7.47 (m, 2H, Ph); $^{31}$P NMR (C$_6$D$_6$) δ93.0.

EXAMPLE 13

Ruthenium complex [(2-methylallyl)$_2$Ru-(1,2-Bis((2R,5R)-2,5-diethylphospholano)benzene)]

This complex was prepared as described above in Example 12, with the exception that the diphospholane 1,2-bis((2R,5R)-2,5-diethylphospholano)benzene prepared as in Example 5 was used. Recrystallization of the product from diethyl ether/methanol at –30° C. afforded the product as an off-white solid which was filtered, washed with cold MeOH, and dried in vacuo. $^1$H NMR (C$_6$D$_6$) δ0.5 (t, J$_{HH}$=6.7 Hz, 6H, CH$_3$), 0.5–1.7 (m, 16H), 1.45 (t, J$_{HH}$=7.4 Hz, 6H, CH$_3$), 1.65 (s, 2H, CH), 1.7–2.2 (m, 6H), 2.20 (s, 6H, CH$_3$), 2.40 (m, 2H, CH, CH$_2$), 2.75 (s, 1H, CH), 7.05 (m, 2H, Ph), 7.50 (m, 2H, Ph); $^{31}$P NMR (C$_6$D$_6$) δ91.8.

EXAMPLE 14

Ruthenium complex
[(2-methylallyl)$_2$Ru-(1,2-Bis((2R,5R)-
2,5-diisopropylphospholano)ethane)]

This complex was prepared as described above in Example 12, with the exception that the diphospholane 1,2-bis((2R,5R)-2,5-diisopropylphospholano) ethane prepared as in Example 7 was used. Recrystallization of the product from diethyl ether/methanol at −30° C. afforded the product as an off-white solid which was filtered, washed with cold MeOH, and dried in vacuo. $^1$H NMR (C$_6$D$_6$) δ0.74 (d, J$_{HH}$=6.8 Hz, 6H, CH$_3$), 0.80–1.30 (m, 12H, CH$_2$), 0.81 (d, J$_{HH}$=6.6 Hz, 6H, CH$_3$), 0.95 (d, J$_{HH}$=6.8 Hz, 6H, CH$_3$), 0.98 (d, J$_{HH}$=6.8 Hz, 6H, CH$_3$), 1.40 (br, 2H, CH$_2$), 1.50–1.75 (m, 6H, CH, CH$_2$), 1.95 (m, 2H, CH), 2.10 (s, 6H, CH$_3$), 2.15 (s, 2H), 2.50 (br, 4H); $^{31}$P NMR (C$_6$D$_6$) δ87.4.

EXAMPLE 15

Rhodium complex [(COD)Rh(1,2-Bis((2R,5R)-
2,5-diethylphosopholano)benzene)]$^+$CF$_3$SO$_3^-$ To [(COD)$_2$Rh]$^+$CF$_3$SO$_3^-$ (0.13 g, 0.28 mmol, COD=1, 5-cyclooctadiene) in THF (10 mL) at 25° C. was added dropwise a solution of 1,2-Bis((2R,5R)-2,5-diethylphospholano)-benzene prepared as in Example 5 (0.10 g, 0.28 mmol) in THF (5 mL). The solution turned orange from yellow upon the phosphine addition. The reaction was allowed to stir for 15 min, and then Et$_2$O (30 mL) was slowly added to. the solution to produce an orange microcrystalline precipitate which was filtered, washed with Et$_2$O, and briefly dried. The solids were dissolved in CH$_2$Cl$_2$ (5 mL), filtered, and Et$_2$O (30 mL) was added slowly to the orange filtrate to provide the titled product as an orange microcrystalline solid (0.112 g, 56%): $^1$H NMR (CD$_2$Cl$_2$) δ0.86 (t, J$_{HH}$=7.3 Hz, 6H, CH$_3$), 1.02 (t, J$_{HH}$=7.3 Hz, 6H, CH$_3$), 1.2–1.6 (m, 6H, CH$_2$), 1.85 (m, 4H, CH, CH$_2$), 2.20 (m, 2H, CH, CH$_2$), 2.20–2.70 (m, 14H, CH$_2$, CH), 4.90 (m (br), 2H, COD-CH), 5.60 (m (br), 2H, COD-CH), 7.70 (m, 4H, Ph); $^{31}$P NMR (CD$_2$Cl$_2$) δ69.5 (d, J$_{RhP}$=148.3 Hz).

EXAMPLE 16

Rhodium complex [(COD)Rh(1,2-Bis((2S,5S)-
2,5-dimethylphospholano)benzene)]$^+$CF$_3$SO$_3^-$ This complex was prepared in a manner analogous to that described above in Example 15 with the exception that the diphospholane 1,2-Bis((2S,5S)-2,5dimethylphospholano)benzene was used. $^1$H NMR (CD$_2$Cl$_2$) δ1.01 (dd, J$_{HH}$=6.8 Hz, J$_{PH}$=15.0 Hz, 6H, CH$_3$), 1.45 (dd, J$_{HH}$=7.1 Hz, J$_{PH}$=18.2 Hz, 6H, CH$_3$), 1.55 (m, 2H, CH$_2$), 1.95 (m, 2H, CH, CH$_2$), 2.20–2.60 (m, 12H, CH$_2$, CH), 2.65 (m, 2H, CH, CH$_2$), 2.75 (m, 2H, CH, CH$_2$), 5.05 (br, 2H, COD-CH), 5.62 (br, 2H, COD-CH), 7.75 (m, 4H, Ph); $^{31}$P NMR (CD$_2$Cl$_2$) δ76.3 (d, J$_{RhP}$=148.7 Hz).

EXAMPLE 17

Rhodium complex [(COD)Rh(1,2-Bis((2R,5R)-2,5-diisopropylphospholano)benzene)]$^+$CF$_3$SO$_3^-$ This complex was prepared in a manner analogous to that described above in Example 15 with the exception that the diphospholane 1,2-Bis((2R,5R)-2,5-diisopropylphospholano)benzene was used. $^1$H NMR (CD$_2$Cl$_2$) δ0.72 (d, J$_{HH}$=6.6 Hz, 6H, CH$_3$), 0.73 (d, J$_{HH}$=6.7 Hz, 6H, CH$_3$), 1.13 (d, J$_{HH}$=6.5 Hz, 6H, CH$_3$), 1.14 (d, J$_{HH}$=6.6 Hz, 6H, CH$_3$), 1.60 (m, 4H, CH$_2$), 1.95 (m, 4H, CH, CH$_2$), 2.15 (m, 2H, CH$_2$), 2.20–2.45 (m, 6H, CH$_2$, CH), 2.45–2.70 (m, 8H, CH, CH$_2$), 4.95 (br, 2H, COD-CH), 5.60 (br, 2H, COD-CH), 7.65 (m, 2H, Ph), 7.75 (m, 2H, Ph); $^{31}$P NMR (CD$_2$Cl$_2$) δ65.5 (d, J$_{RhP}$=148.5 Hz).

EXAMPLE 18

Rhodium complex [(COD)Rh(1,2-Bis((2R,5R)-2,5-diisopropylphosphlano)ethane]$^+$CF$_3$SO$_3^-$ This complex was prepared in a manner analogous to that described above in Example 15 with the exception that the diphospholane 1,2-Bis((2R,5R)-2,5-diisopropylphospholano)ethane was used. $^1$H NMR (CD$_2$Cl$_2$) δ0.97 (d, J$_{HH}$=6.6 Hz, 6H, CH$_3$), 0.90–1.20 (m, 2H, CH$_2$), 1.10 (d, J$_{HH}$=6.6 Hz, 6H, CH$_3$), 1.15 (d, J$_{HH}$=6.5 Hz, 6H, CH$_3$), 1.40 (d, J$_{HH}$=6.5 Hz, 6H, CH$_3$), 1.30–1.50 (m, 4H, CH$_2$), 1.50–2.00 (m, 10H, CH, CH$_2$), 2.00–2.60 (m, 12H, CH), 4.85 (m (br), 2H, COD-CH), 5.30 (m (br), 2H, COD-CH); $^{31}$P NMR (CD$_2$Cl$_2$) δ65.2 (d, J$_{RhP}$=145.2 Hz).

EXAMPLE 19

Rhodium complex [(COD)Rh(1,2-Bis((2R,5R)-2,5-diethylphospholano)ethane)]$^+$CF$_3$SO$_3^-$ This complex was prepared in an analogous manner to that described above as in Example 15. $^1$H NMR (CD$_2$Cl$_2$) δ1.07 (t, J$_{HH}$=7.3 Hz, 6H, CH$_3$), 1.13 (t, J$_{HH}$=7.3 Hz, 6H, CH$_3$), 1.20–1.50 (m, 8H, CH$_2$), 1.50–2.10 (m, 12H, CH, CH$_2$), 2.15–2.60 (m, 12H, CH, CH$_2$), 4.85 (m (br), 2H, COD-CH), 5.30 (m (br), 2H, COD-CH), 7.70 (m, 4H, Ph); $^{31}$P NMR (CD$_2$Cl$_2$) δ71.2 (d, J$_{RhP}$=145.3 Hz).

EXAMPLE 20

Asymmetric Hydrogenations: General Procedure

In a dry box, a 100 mL Fisher-Porter tube was charged with 0.25–0.35M methanol solution of substrate, anhydrous, degassed MeOH or THF (20 mL), and catalyst precursor (0.1 mol %). After four vaccum/H$_2$ cycles, the tube was pressurized to an initial pressure of 30 psig H$_2$ (Matheson, 99.998%). The reactions were allowed to stir at 20°–25° C. until no further hydrogen uptake was observed. Complete (100%) conversion to product was indicated by GC and $^1$H NMR analyses, unless otherwise noted. Reaction time for complete (100%) conversion was 1–2 h. The reactions were concentrated, and the residue passed through a short SiO$_2$ column (EtOAC/hexane or Et$_2$O/pentane, 50/50) to afford the products. Product absolute configurations were established by sign of optical rotations.

Enantiomeric Excess Determinations

Enantiomeric excesses listed are the average value obtained from 2–3 experiments. Enantiomeric excesses were determined as follows: N-acetylphenylalanine methyl ester (HPLC, Daicel Chiralcel OJ, 1.0 mL/min, 10% 2-PrOH/ hexane) (R) $t_1$ 8.9 min; (S) $t_2$ 11.4 min); N-methyl ester (Capillary GC, Chrompack XE-60-S-Valine-S-α-phenylethylamide, 155° C. isothermal) (R) $t_1$ 10.69 min, (S) $t_2$ 11.21 min; N-acetylleucine methyl ester (Capillary GC, Chrompack XE-60-S-Valine-S-α-phenylethylamide, 160° C. isothermal) (R) $t_1$ 16.49 min, (S) $t_2$ 17.48 min; N-benzoylphenylalanine methyl ester (HPLC, Daicel Chiralcel OJ, 1.0 mL/min, 10% 2-PrOH/hexane) (R) $t_1$ 10.1 min; (S) $t_2$ 13.4 min); dimethyl 2-methylsuccinate (500 MHz$^1$H NMR in CDCl$_3$, chiral shift reagent (+)-Eu(hfc)$_3$), baseline resolution of ester methoxyl resonance at δ3.69 observed at Δδ0.25; 1-acetoxy-1-phenylethane derivatives (Capillary GC, J & W Cyclodex-B): Ph=C$_6$H$_5$ (160° C. isothermal) (S) $t_1$ 7.66 min, (R) $t_2$ 7.92 min; Ph=p-FC$_6$H$_4$ (120° C. isothermal) $t_1$ 7.89 min, $t_2$ 8.15 min; Ph=m-FC$_6$H$_4$ (120° C. isothermal) $t_1$ 7.33 min, $t_2$ 7.61 min; Ph=m-C$_1$ClH$_4$ (130° C. isothermal) $t_1$ 12.44 min, $t_2$ 12.80 min; Ph=p-NO$_2$C$_6$H$_4$ (500 MHz$^1$H NMR in CDCl$_3$, chiral shift reagent (+)-Eu(hfc)$_3$), baseline resolution of acetoxy methyl resonance at δ8 2.15 observed at Δδ1.2; 1-acetoxy-1-(1-naphthyl)ethane (HPLC on alcohol obtained by hydrolysis with NaOMe/MeOH, Daicel Chiralcel OJ, 1.0 mL/min, 10% 2-PrOH/hexane) $t_1$ 9.48 min, $t_2$ 13.53 min; ethyl O-acetyllactate (by comparison with optical rotation of authentic product (S)-(−)-O-Acetyllactate $[\alpha]_D^{25}$=−50.6° (c 1.0, CHCl$_3$); combined with $^1$H NMR to assure reduction product purity); 1,1,1-trifluoro-2-acetoxypropane (500 MHz$^1$H NMR in CDCl$_3$, chiral shift reagent (+)-Eu(hfc)$_3$), baseline resolution of acetoxy methyl resonance at δ1.60 observed at Δδ0.6.

Absolute Configurations

Hydrogenation product absolute configurations were established by comparison of the sign of optical rotation with that of the configurationally assigned compound. The following referenced compounds were used for comparison: (S)-N-acetylphenylalanine methyl ester $[\alpha]_D^{20}$=+16.4° (c 2, MeOH); (S)-N-acetylalanine methyl ester $[\alpha]_D^{23}$=−91.7° (c 2, H$_2$O); (S)-N-acetylleucine methyl ester $[\alpha]D^{17}$=−42.0° (c 3.3, MeOH); (S)-N-benzoylphenylalanine methyl ester $[\alpha]_D^{25}$=−45.3° (c 1, MeOH); (R)-dimethyl 2-methylsuccinate ($[\alpha]_D^{25}$=+6.11° (neat); (S)-1-acetoxy-1-phenylethane ($[\alpha]_D^{21}$=−130.5° (c 3, benzene); (R)-(+)-1-acetoxy-1-(p-nitrophenyl)ethane; (S)-1-hydroxy-1-(1-naphthyl)ethane $([\alpha]_D^{21}$=−78.9° (c 5, EtOH); ethyl O-acetyllactate (by comparison with optical rotation of authentic product (S)-(−)-O-Acetyllactate $[\alpha]_D^{25}$=−50.6° (c 1.0, CHCl$_3$); (S)-1,1,1-trifluoro-2-acetoxypropane ($[\alpha]_D^{23}$=+18.7° (neat)$^{14}$;

Asymmetric Hydrogenation of Methyl
(Z)-α-acetamidocinnamate

A 100 mL Fisher-Porter tube was charged with methyl (Z)-α-acetamidocinnamate (300 mg, 1.36 mmol), rhodium catalyst [(COD)Rh(1,2-Bis((2R,5R)-2,5-diethylphospholano)benzene)]$^+$CF$_3$SO$_3^-$ prepared as in Example 15 (1.0 mg, 0.00136 mmol), MeOH (6.0 mL), and a stir bar. After sealing, the pressure head was then connected to a hydrogen tank (Matheson, 99.998%) and the lines were purged of air by four vacuum/H$_2$ cycles. After two vacuum/H$_2$ cycles on the reaction mixture, the tube was pressurized to an initial pressure of 30 psig H$_2$. The reaction was allowed to stir at 20° C. for 2 h after which no further H$_2$ uptake was observed. Complete conversion to product was indicated by capillary GC (methyl silicone column). The reaction was concentrated on a rotovap and the residue was chromatographed on a short SiO$_2$ column (ca. 6×0.5 cm) using 80% ethyl acetate/hexane as eluent. The fractions containing product were concentrated on a rotovap to give methyl (R)-N-acetylphenylalanine as a colorless crystalline solid (270 mg, 90%). Enantiomeric excess analysis by HPLC using Daicel Chiralcel OJ column as described above indicated 99% enantiomeric purity. Other substrates were hydrogenated using the above procedure and the resulting data is summarized in Tables 1 and 2.

TABLE 1

Asymmetric Hydrogenation of Acetamidoacrylates

| | (% ee) Substrate | | |
|---|---|---|---|
| Complexes | Ph-C(CO$_2$Me)=C-N(H)Ac | iPh-C(CO$_2$Me)=C-N(H)Ac | C(CO$_2$Me)=C-N(H)Ac |
| A$^a$ | 85 | 64.4 | 91.4 |
| Example 19 | 93 | 81.2 | 98.1 |
| Example 18 | 93 | 98.8 | 96.4 |
| Example 16 | 98 | 95.2 | 99.0 |
| Example 15 | 99 | 99.0 | 99.4 |
| Example 17 | 87 | 96.9 | 95.4 |

$^a$Sample A represents a ligand of high enantiomeric purity of formula VII wherein R is methyl complexed with [(COD)$_2$Rh]$^+$CF$_3$SO$_3^-$ using the process of Example 15.

TABLE 2

Asymmetric Hydrogenation of Enol Acetates $$\underset{R}{\overset{H}{\underset{OAc}{\diagup}}}\hspace{-1em}\diagdown\hspace{-1em}\overset{H}{\diagup} \xrightarrow{H_2} \underset{R}{\overset{CH_3}{\diagup}}\hspace{-1em}\overset{H}{\diagdown}\hspace{-1em}\underset{OAc}{}$$

| R | Complexes | Previous Best$^a$ | % ee (configuration) |
|---|---|---|---|
| C$_6$H$_5$ | Example 16 | 64 | 89 (−)-(S) |
| p-NO$_2$C$_6$H$_4$ | Example 19 | 65 | 90 (+)-(R) |
| m-ClC$_6$H$_4$ | Example 15 | — | 91 (+)$^b$ |
| p-FC$_6$H$_4$ | Example 19 | — | 89 (+)$^b$ |
| m-FC$_6$H$_4$ | Example 15 | — | 89 (+)$^b$ |
| 1-Naphthyl | Example 19 | — | 94 (+)-(R) |
| 1-Naphthyl | Example 16 | — | 93 (−)-(S) |
| CO$_2$Et | Example 16 | 89 | 99 (−)-(S) |
| CO$_2$Et | Example 15 | 89 | >99 (+)-(R) |
| CO$_2$Et | Example 19 | 89 | >99 (+)-(R) |
| CF$_3$ | Example 16 | 77 | 94 (+)-(S) |
| CF$_3$ | Example 19 | 77 | >95 (−)-(R) |

$^a$Values listed denote highest ee's previously reported for catalytic asymmetric hydrogenation of these substrates in Koenig, K. E.; Bachman, G. L.; Vineyard, B. D., J. Org. Chem., 1980, 45, 2362, and Selke, R.; Pracejus, H., J. Mol. Cat., 1986, 37,213.
$^b$Absolute configuration not established.

EXAMPLE 21

Ruthenium-catalyzed asymmetric hydrogenation of 2-methyl-2-butenoic acid

The hydrogenation of 2-methyl-2-butenoic acid was carried out in a Fisher-Porter tube at 20°–25° C. in 0.67M methanol solutions of substrate under initial hydrogen pressure 60 psi (4 atm). The catalyst was prepared in situ by reacting the precursor complex [(COD)Ru(2-methylallyl)$_2$] (Lewis et al., J. Chem. Soc., Dalton, 1974, 951; Powell and Shaw, J. Chem. Soc. (A), 1968, 159) each herein incorporated by reference, with 1.1 equivalents of phosphine in diethyl ether solution. An aliquot of this preformed catalyst solution was then added directly to a methanol solution of 2-methyl-2-butenoic acid, and the mixture then placed under hydrogen pressure. The reactions were allowed to stir for 12 h, after which no further hydrogen uptake was observed. Product isolation and enantiomeric excess determination was carried out as described below.

To a solution of [(COD)Ru(2-methylallyl)$_2$] (10 mg, 0.031 mmol) in diethyl ether (0.5 mL) was added a solution of 1,2-bis((2R,5R)-2,5-diisopropylphospholano)benzene (15 mg, 0.035 mmol) in diethyl ether (0.5 mL). A Fisher-Porter tube was charged with a stir bar, methanol (6.0 mL), 2-methyl-2-butenoic acid (0.4 g, 4.0 mmol), and 0.1 mL of the catalyst solution prepared above in diethyl ether. After sealing, the pressure head was then connected to a hydrogen tank (Matheson, 99.998%) and the lines were purged of air by four vacuum/H$_2$ cycles. After two vacuum/H$_2$ cycles on the reaction mixture, the tube was pressurized to an initial pressure of 60 psig H$_2$. The reaction was allowed to stir at 20° C. for 12 h after which no further H$_2$ uptake was observed. Complete conversion to product was indicated by capillary GC (methyl silicone column). The reaction was concentrated on a rotovap and the residue was dissolved in methylene chloride (20 mL). The organic layer was then extracted once with 1N sodium hydroxide solution. If necessary, the aqueous layer was filtered. The aqueous layer then was acidified with concentrated HCl to pH=1. The resulting mixture was extracted with diethyl ether (3×30 mL) and the organic layer dried over magnesium sulfate. Filtration and concentration on a rotovap provided the product, (S)-(+)-2-methylbutanoic acid, as a colorless oil (0.35 g, 88%). The enantiomeric excess was determined by comparison of the obtained optical rotation with that of authentic (S)-(+)-2-methylbutanoic acid ([α]$_D^{25}$=+19.9° (c 1, hexane)). Observed [α]$_D^{25}$=+18.6° (c 1, hexane) which indicated an enantiomeric excess of 93% ee. Hydrogenations of 2-methyl-2-butenoic acid using catalysts derived from other phosphines were carried out in an analogous fashion. Data are summarized in Table 3.

TABLE 3

Ruthenium-catalyzed Asymmetric
Hydrogenation of 2-Methyl-2-butenoic acid $$\text{CO}_2\text{H structure} \xrightarrow[\substack{\text{MeOH} \\ \text{H}_2 \text{ (60 psi)} \\ 12 \text{ h}}]{\text{Ru catalyst}} \text{CO}_2\text{H structure}$$

| Ligand | % ee |
| --- | --- |
| Example 4 | 78% ee (S) |
| Example 5 | 88% ee (R) |
| Example 8 | 93% ee (S) |

What is claimed is:

1. A chiral ligand of formula Vc:

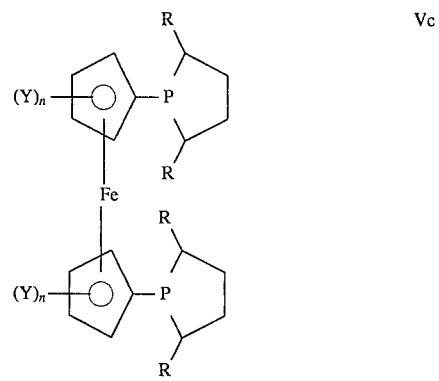

wherein:

R is a radical selected from the group consisting of alkyl, fluoroalkyl or perfluoroalkyl, each containing up to about 8 carbon atoms; aryl; aralkyl; or —CR'$_2$(CR'$_2$)$_q$X(CR'$_2$)$_p$R';

q and p are each integers, the same or different, ranging from 1 to about 8;

R' is H; F; aryl; or alkyl, fluoroalkyl or perfluoroalkyl, each containing up to about 8 carbon atoms;

X is O, S, NR", PR", divalent aryl, or divalent fused aryl;

R" is hydrogen; alkyl, fluoroalkyl or perfluoroalkyl, each containing up to about 8 carbon atoms; aryl; aralkyl; or —CR'$_2$(CR'$_2$)$_q$Z(CR'$_2$)$_p$R';

Z is O, S, NR', or PR'; and each Y is independently hydrogen, halogen, alkyl, alkoxy, aryl, aryloxy, nitro, amino, vinyl, substituted vinyl, alkynyl or sulfonic acid, and n is an integer from 1 to 6 equal to the number of unsubstituted aromatic ring carbons.

2. A chiral ligand of claim 1 wherein R is methyl, ethyl or isopropyl and Y is hydrogen.

3. A chiral ligand of claim 1 having a high degree of enantiomeric purity.

4. A chiral ligand of claim 1 which is 1,1'-bis(2,5-diethylphospholano)ferrocene.

5. A chiral ligand of claim 1 which is 1,1'-bis((2R,5R)-2,5-diethylphospholano)ferrocene or the (2S,5S) analog thereof.

* * * * *